United States Patent
Cholli et al.

(10) Patent No.: US 8,846,847 B2
(45) Date of Patent: *Sep. 30, 2014

(54) MACROMOLECULAR ANTIOXIDANTS BASED ON STERICALLY HINDERED PHENOLS AND PHOSPHITES

(71) Applicant: Polnox Corporation, Lowell, MA (US)

(72) Inventors: Ashok L. Cholli, Lowell, MA (US); Rajesh Kumar, Groton, CT (US)

(73) Assignee: Polnox Corporation, Lowell, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/904,755

(22) Filed: May 29, 2013

(65) Prior Publication Data

US 2014/0014880 A1 Jan. 16, 2014

Related U.S. Application Data

(60) Continuation of application No. 13/575,884, filed on Aug. 13, 2012, now Pat. No. 8,598,382, which is a continuation of application No. 13/109,800, filed on May 17, 2011, now Pat. No. 8,242,230, which is a division of application No. 12/789,843, filed on May 28, 2010, now Pat. No. 7,956,153, which is a continuation of application No. 11/293,844, filed on Dec. 2, 2005, now Pat. No. 7,902,317.

(60) Provisional application No. 60/633,196, filed on Dec. 3, 2004.

(51) Int. Cl.
| | |
|---|---|
| C08G 63/00 | (2006.01) |
| C08K 5/20 | (2006.01) |
| C08K 13/02 | (2006.01) |
| C08G 61/10 | (2006.01) |
| C08G 61/00 | (2006.01) |
| C09K 15/32 | (2006.01) |
| C08K 5/04 | (2006.01) |
| C07C 231/02 | (2006.01) |
| C08K 5/52 | (2006.01) |

(52) U.S. Cl.
CPC ...... *C09K 15/322* (2013.01); *C08G 2261/1422* (2013.01); *C08G 2261/1432* (2013.01); *C08K 5/20* (2013.01); *C08K 13/02* (2013.01); *C08G 61/10* (2013.01); *C08G 2261/1426* (2013.01); *C08G 61/00* (2013.01); *C08K 5/04* (2013.01); *C07C 231/02* (2013.01); *C08K 5/52* (2013.01)
USPC ............ 528/183; 528/86; 528/184; 528/211; 528/223

(58) Field of Classification Search
USPC .................. 528/86, 183, 184, 211
See application file for complete search history.

(56) References Cited

U.S. PATENT DOCUMENTS

| | | |
|---|---|---|
| 3,116,305 A | 12/1963 | Morris et al. |
| 3,294,836 A | 12/1966 | Peterson et al. |
| 3,441,545 A | 4/1969 | Blatz et al. |
| 3,459,704 A | 8/1969 | Peterson et al. |
| 3,557,245 A | 1/1971 | Phillips et al. |
| 3,632,785 A | 1/1972 | Bornstein |
| 3,645,970 A | 2/1972 | Kleiner |
| 3,649,667 A | 3/1972 | Song et al. |
| 3,655,831 A | 4/1972 | Friedman |
| 3,870,680 A | 3/1975 | Schurdak |
| 3,907,939 A | 9/1975 | Robin et al. |
| 3,953,402 A | 4/1976 | Kline |
| 3,965,039 A | 6/1976 | Chaplits et al. |
| 3,983,091 A | 9/1976 | Gloth et al. |
| 3,994,828 A | 11/1976 | Zaffaroni |
| 3,996,160 A | 12/1976 | Dale et al. |
| 3,996,198 A | 12/1976 | Wang et al. |

(Continued)

FOREIGN PATENT DOCUMENTS

| | | |
|---|---|---|
| CS | 111291 | 6/1964 |
| DE | 197 47 644 A1 | 5/1999 |

(Continued)

OTHER PUBLICATIONS

U.S. Appl. No. 12/082,967: Notice of Allowance mailed Jan. 27, 2010; Title: Stabilized Polyolefin Composition.

(Continued)

*Primary Examiner* — Gregory Listvoyb
(74) *Attorney, Agent, or Firm* — Hamilton, Brook, Smith & Reynolds, P.C.

(57) ABSTRACT

A sterically hindered phenol and phosphite based compound represented the following formula:

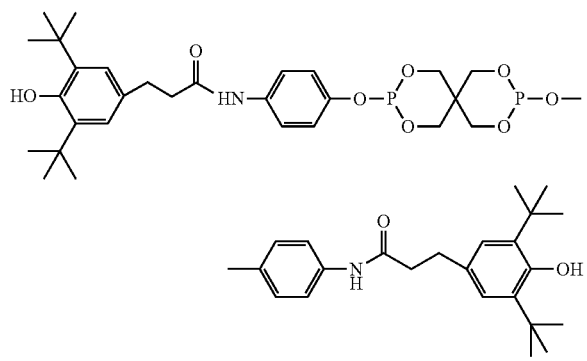

and its use as an antioxidant in a wide range of materials including, but not limited to, food, plastics, elastomers, composites and petroleum based products is disclosed herein.

1 Claim, 4 Drawing Sheets

(56) References Cited

U.S. PATENT DOCUMENTS

| | | |
|---|---|---|
| 4,054,676 A | 10/1977 | Weinshenker et al. |
| 4,094,857 A | 6/1978 | Wolfe, Jr. |
| 4,096,319 A | 6/1978 | Willette et al. |
| 4,097,464 A | 6/1978 | Kline |
| 4,098,829 A | 7/1978 | Weinshenker et al. |
| 4,107,144 A | 8/1978 | Russell et al. |
| 4,136,055 A | 1/1979 | Lyons |
| 4,202,816 A | 5/1980 | Moser et al. |
| 4,205,151 A | 5/1980 | Dale et al. |
| 4,213,892 A | 7/1980 | Scott |
| 4,219,453 A | 8/1980 | Sakurai et al. |
| 4,267,358 A | 5/1981 | Hechenbleikner et al. |
| 4,281,192 A | 7/1981 | Jacquet et al. |
| 4,283,572 A | 8/1981 | Klicker |
| 4,317,933 A | 3/1982 | Parker |
| 4,341,879 A | 7/1982 | Sugio et al. |
| 4,355,148 A | 10/1982 | Layer et al. |
| 4,377,666 A | 3/1983 | Farrar |
| 4,380,554 A | 4/1983 | Serres, Jr. |
| 4,447,657 A | 5/1984 | Firth et al. |
| 4,465,871 A | 8/1984 | Firth et al. |
| 4,510,296 A | 4/1985 | Hergenrother |
| 4,511,491 A | 4/1985 | Ishii et al. |
| 4,634,728 A | 1/1987 | Dunski et al. |
| 4,690,995 A | 9/1987 | Keskey et al. |
| 4,761,247 A | 8/1988 | Rei et al. |
| 4,824,929 A | 4/1989 | Arimatsu et al. |
| 4,849,503 A | 7/1989 | Cotter et al. |
| 4,855,345 A | 8/1989 | Rosenberger et al. |
| 4,857,596 A | 8/1989 | MacLeay et al. |
| 4,870,214 A | 9/1989 | Mina et al. |
| 4,894,263 A | 1/1990 | Dubois et al. |
| 4,897,438 A | 1/1990 | Kikuchi et al. |
| 4,900,671 A | 2/1990 | Pokora et al. |
| 4,925,591 A | 5/1990 | Nakauchi et al. |
| 4,968,759 A | 11/1990 | Kikuchi et al. |
| 4,977,004 A | 12/1990 | Bettle, III et al. |
| 4,981,917 A | 1/1991 | MacLeay et al. |
| 4,994,628 A | 2/1991 | Goddard et al. |
| 5,013,470 A | 5/1991 | Benfaremo |
| 5,017,727 A | 5/1991 | Olivier |
| 5,082,358 A | 1/1992 | Tabata et al. |
| 5,102,962 A | 4/1992 | Kikuchi et al. |
| 5,117,063 A | 5/1992 | Stern et al. |
| 5,143,828 A | 9/1992 | Akkara et al. |
| 5,155,153 A | 10/1992 | Neri et al. |
| 5,185,391 A | 2/1993 | Stokich, Jr. |
| 5,185,407 A | 2/1993 | Wong |
| 5,188,953 A | 2/1993 | Johnson et al. |
| 5,191,008 A | 3/1993 | Frost et al. |
| 5,196,142 A | 3/1993 | Mollet et al. |
| 5,206,303 A | 4/1993 | Tse et al. |
| 5,207,939 A | 5/1993 | Farng et al. |
| 5,274,060 A | 12/1993 | Schadeli |
| 5,278,055 A | 1/1994 | Cyrus, Jr. et al. |
| 5,304,589 A | 4/1994 | Davidson et al. |
| 5,320,889 A | 6/1994 | Bettle, III |
| 5,449,715 A | 9/1995 | Plochocka et al. |
| 5,498,809 A | 3/1996 | Emert et al. |
| RE35,247 E | 5/1996 | Cyrus, Jr. et al. |
| 5,516,856 A | 5/1996 | Sanchez |
| 5,541,091 A | 7/1996 | Wheeler et al. |
| 5,565,300 A | 10/1996 | Uenishi et al. |
| 5,574,118 A | 11/1996 | Olivier |
| 5,652,201 A | 7/1997 | Papay et al. |
| 5,739,341 A | 4/1998 | Dubs et al. |
| 5,834,544 A | 11/1998 | Lin et al. |
| 5,837,798 A | 11/1998 | Hutchings et al. |
| 5,869,592 A | 2/1999 | Gagne et al. |
| 5,911,937 A | 6/1999 | Hekal |
| 5,994,498 A | 11/1999 | Tripathy et al. |
| 6,018,018 A | 1/2000 | Samuelson et al. |
| 6,046,263 A | 4/2000 | Rasberger et al. |
| 6,096,695 A | 8/2000 | Lam et al. |
| 6,096,859 A | 8/2000 | Akkara et al. |
| 6,150,491 A | 11/2000 | Akkara |
| 6,232,314 B1 | 5/2001 | Jarrott et al. |
| 6,342,549 B1 | 1/2002 | Hirose et al. |
| 6,444,450 B2 | 9/2002 | Akkara et al. |
| 6,646,035 B2 | 11/2003 | Koch et al. |
| 6,723,815 B2 | 4/2004 | Callaghan et al. |
| 6,743,525 B2 | 6/2004 | Bernsten et al. |
| 6,770,785 B1 | 8/2004 | Desai et al. |
| 6,794,480 B2 | 9/2004 | Goto et al. |
| 6,800,228 B1 | 10/2004 | Semen |
| 6,828,364 B2 | 12/2004 | Gugumus |
| 6,846,859 B2 * | 1/2005 | Coffy et al. .................. 524/128 |
| 7,132,496 B2 | 11/2006 | Kerres et al. |
| 7,169,844 B2 | 1/2007 | Inokami |
| 7,205,350 B2 | 4/2007 | Thibaut |
| 7,223,432 B2 | 5/2007 | Cholli et al. |
| 7,262,319 B2 | 8/2007 | Rehm et al. |
| 7,705,176 B2 | 4/2010 | Cholli et al. |
| 7,705,185 B2 | 4/2010 | Kumar et al. |
| 7,902,317 B2 | 3/2011 | Kumar et al. |
| 7,956,153 B2 | 6/2011 | Cholli et al. |
| 8,008,423 B2 | 8/2011 | Kumar et al. |
| 8,039,673 B2 | 10/2011 | Cholli et al. |
| 8,080,689 B2 | 12/2011 | Kumar |
| 8,242,230 B2 | 8/2012 | Cholli et al. |
| 8,252,884 B2 | 8/2012 | Kumar et al. |
| 8,481,670 B2 | 7/2013 | Kumar et al. |
| 8,598,382 B2 | 12/2013 | Cholli et al. |
| 2001/0041203 A1 | 11/2001 | Uno et al. |
| 2002/0007020 A1 | 1/2002 | Higahimura et al. |
| 2002/0128493 A1 | 9/2002 | Romanczyk, Jr. et al. |
| 2002/0143025 A1 | 10/2002 | Pratt et al. |
| 2002/0183470 A1 | 12/2002 | Tripathy et al. |
| 2003/0030033 A1 | 2/2003 | Duyck et al. |
| 2003/0078346 A1 | 4/2003 | Nakamura et al. |
| 2003/0091837 A1 | 5/2003 | Aoki |
| 2003/0176620 A1 | 9/2003 | Romanczyk, Jr. et al. |
| 2003/0191242 A1 | 10/2003 | Zedda et al. |
| 2003/0229196 A1 | 12/2003 | Braat et al. |
| 2003/0230743 A1 | 12/2003 | Cholli et al. |
| 2004/0015021 A1 | 1/2004 | Adams et al. |
| 2004/0164279 A1 | 8/2004 | Stevenson et al. |
| 2004/0180994 A1 | 9/2004 | Pearson et al. |
| 2004/0186167 A1 | 9/2004 | Dou et al. |
| 2004/0186214 A1 | 9/2004 | Li et al. |
| 2004/0198875 A1 | 10/2004 | Kaprinidis et al. |
| 2004/0214935 A1 | 10/2004 | Cholli et al. |
| 2005/0170978 A1 | 8/2005 | Migdal et al. |
| 2005/0209379 A1 | 9/2005 | Botkin et al. |
| 2005/0238789 A1 | 10/2005 | Cholli et al. |
| 2005/0242328 A1 | 11/2005 | Baranski |
| 2006/0029706 A1 | 2/2006 | Cholli et al. |
| 2006/0040833 A1 | 2/2006 | Al-Akhdar et al. |
| 2006/0041087 A1 | 2/2006 | Cholli |
| 2006/0041094 A1 | 2/2006 | Cholli |
| 2006/0128929 A1 | 6/2006 | Yang et al. |
| 2006/0128930 A1 | 6/2006 | Dhawan et al. |
| 2006/0128931 A1 | 6/2006 | Kumar et al. |
| 2006/0128939 A1 | 6/2006 | Kumar et al. |
| 2006/0154818 A1 | 7/2006 | Destro et al. |
| 2006/0189820 A1 | 8/2006 | Rehm et al. |
| 2006/0189824 A1 | 8/2006 | Kumar et al. |
| 2006/0208227 A1 | 9/2006 | Shiraki |
| 2006/0233741 A1 | 10/2006 | Kumar et al. |
| 2007/0010632 A1 | 1/2007 | Kaplan et al. |
| 2007/0106059 A1 | 5/2007 | Cholli et al. |
| 2007/0135539 A1 | 6/2007 | Cholli et al. |
| 2007/0149660 A1 | 6/2007 | Kumar et al. |
| 2007/0154430 A1 | 7/2007 | Cholli et al. |
| 2007/0154608 A1 | 7/2007 | Cholli et al. |
| 2007/0154720 A1 | 7/2007 | Cholli et al. |
| 2007/0161522 A1 | 7/2007 | Cholli et al. |
| 2008/0249335 A1 | 10/2008 | Cholli et al. |
| 2008/0293856 A1 | 11/2008 | Kumar et al. |
| 2008/0311065 A1 | 12/2008 | Cholli |
| 2009/0184294 A1 | 7/2009 | Cholli et al. |
| 2011/0040125 A1 | 2/2011 | Kumar et al. |
| 2011/0282098 A1 | 11/2011 | Cholli et al. |
| 2012/0004150 A1 | 1/2012 | Cholli et al. |

(56) References Cited

U.S. PATENT DOCUMENTS

| | | |
|---|---|---|
| 2012/0071596 A1 | 3/2012 | Kumar et al. |
| 2012/0123145 A1 | 5/2012 | Cholli et al. |
| 2012/0142968 A1 | 6/2012 | Kumar et al. |
| 2013/0041171 A1 | 2/2013 | Cholli et al. |
| 2013/0072586 A1 | 3/2013 | Kumar et al. |
| 2013/0130955 A1 | 5/2013 | Cholli et al. |

FOREIGN PATENT DOCUMENTS

| | | | |
|---|---|---|---|
| DE | 198 43 875 | A1 | 3/2000 |
| EP | 0 181 023 | A1 | 5/1986 |
| EP | 0 289 077 | A2 | 11/1988 |
| EP | 0 358 157 | | 3/1990 |
| EP | 0 404 039 | A1 | 12/1990 |
| EP | 0 618 203 | A1 | 10/1994 |
| EP | 0 688 805 | A1 | 12/1995 |
| EP | 1 067 144 | A1 | 1/2001 |
| EP | 1 468 968 | A1 | 10/2004 |
| FR | 2 183 973 | | 1/1974 |
| GB | 1 042 639 | | 8/1964 |
| GB | 1 283 103 | | 7/1972 |
| GB | 1 320 169 | | 6/1973 |
| GB | 1 372 042 | | 10/1974 |
| GB | 1 389 442 | | 4/1975 |
| GB | 1 469 245 | | 4/1977 |
| GB | 1 482 649 | | 8/1977 |
| JP | 69002715 | B | 1/1966 |
| JP | 43016392 | B4 | 7/1968 |
| JP | 43018453 | B | 8/1968 |
| JP | 44024274 | | 10/1969 |
| JP | 44028850 | | 11/1969 |
| JP | 45 2980 | | 1/1970 |
| JP | 49 29339 | | 3/1974 |
| JP | 57085366 | A | 5/1982 |
| JP | 59025814 | | 2/1984 |
| JP | 59197447 | | 11/1984 |
| JP | 60-199832 | | 10/1985 |
| JP | 05 199858 | | 8/1993 |
| JP | 06135876 | A | 5/1994 |
| JP | 06 247959 | | 9/1994 |
| JP | 08027226 | A | 1/1996 |
| JP | 09262069 | | 10/1997 |
| JP | 09 328519 | | 12/1997 |
| JP | 09 328521 | | 12/1997 |
| JP | 9322784 | A | 12/1997 |
| JP | 11-80063 | | 3/1999 |
| JP | 11-158103 | | 6/1999 |
| JP | 2003138258 | | 5/2003 |
| NL | 7 905 000 | | 3/1980 |
| WO | WO 92/20734 | | 11/1992 |
| WO | WO 00/39064 | | 7/2000 |
| WO | WO 01/18125 | AI | 3/2001 |
| WO | WO 01/48057 | A1 | 7/2001 |
| WO | WO 02/079130 | A1 | 10/2002 |
| WO | WO 03/087260 | A1 | 10/2003 |
| WO | WO 03/102004 | A1 | 12/2003 |
| WO | WO 2004/024070 | A2 | 3/2004 |
| WO | WO 2004/050795 | A2 | 6/2004 |
| WO | WO 2005/025513 | A2 | 3/2005 |
| WO | WO 2005/025646 | B4 | 3/2005 |
| WO | WO 2005/060500 | A2 | 7/2005 |
| WO | WO 2005/070974 | A2 | 8/2005 |
| WO | WO 2005/071005 | A1 | 8/2005 |
| WO | WO 2006/018403 | A1 | 2/2006 |
| WO | WO 2006/060801 | A2 | 6/2006 |
| WO | WO 2006/104957 | A2 | 10/2006 |
| WO | WO 2008/005358 | A2 | 1/2008 |

OTHER PUBLICATIONS

U.S. Appl. No. 12/082,967: Office Action mailed Aug. 4, 2009; Title: Stabilized Polyolefin Composition.
U.S. Appl. No. 12/082,967: Office Action mailed Jan. 27, 2009; Title: Stabilized Polyolefin Composition.
U.S. Appl. No. 12/082,967: Request for Continued Examination, Amendment and Remarks mailed Jan. 4, 2010; Title: Stabilized Polyolefin Composition.
Akkara, J.A., et al., "Hematin-Catalyzed Polymerization of Phenol Compounds," Macromolecules, 33(7):2377-2382 (2000).
Akkara, J.A., et al., "Synthesis and Characterization of Polymers Produced by Horseradish Peroxidase in Dioxane," J. of Polymer Science: Part A: Polymer Chemistry, 29(11):1561-1574 (1991).
Al-Malaika, S and Suharty, N., "Reactive Processing of Polymers: Mechanisms of Grafting Reactions of Functional Antioxidants on Polyolefins in the Presence of a Coagent," Polymer Degradation and Stability 49: 77-89 (1995).
Armengol, E., et al., "Acid Zeolites as Catalysts in Organic Reactions, tert-Butylation of Anthracene, Naphthalene and Thianthrene," Appl. Catal. A 149:411-423 (1997).
Ayyagari, M.S., et al., "Controlled Free-Radical Polymerization of Phenol Derivatives by Enzyme-Catalyzed Reactions in Organic Solvents," Macromolecules, 28(15):5192-5197 (1995).
Badamali, S.K., et al., "Influence of Aluminium Sources on the Synthesis and Catalytic Activity of Mesoporous A1MCM-41 Molecular Sieves," Catal. Today 63:291-295 (2000).
Belyaev, A., et al., "Structure-Activity Relationship of Diaryl Phosphonate Esters as Potent Irreversible Dipeptidyl Peptidase IV Inhibitors," J. Med. Chem., 42(6):1041-1052 (1998).
Blokhin, Y.I, et al., "Phosphorylation of Dihydric Phenols with Amides of Phosphorous Acid," Russian Chem. Bulletin, 45(9):2250-2251 (1996).
Bruno, F.F., et al., "Enzymatic Template Synthesis of Polyphenol," Materials Research Society Symposium Proceedings vol. 600, Electroactive Polymers (EAP):255-259 (1999).
Chandra, K.G. and Sharma, M.M., "Alkylation of Phenol with MTBE and Other tert-butyl-ethers: Cation Exchange Resins as Catalysts," Catal. Lett. 19(4):309-317 (1993).
Ciric-Marjanovic, et al., Chemical Oxidative Polymerization of Aminodiphenylamines, Journal of Physical Chemistry B, 112, 23: 6976-6987 (2008).
Coppinger, G.B., et al., "Photo-Fries Rearrangement of Aromatic Esters. Role of Steric and Electronic Factors" J. of Phy. Chem., 70(11):3479-3489 (1966).
Database Beilstein [online] Beilstein Institut Zur Förderung Der Chemischen Wissenschaften; XP002420027, Beilstein Registry No. 3517906.
Database Beilstein [online] Beilstein Institut Zur Förderung Der Chemischen Wissenschaften; XP002420028, Beilstein Registry No. 5840042.
Database Beilstein [online] Beilstein Institut Zur Förderung Der Chemischen Wissenschaften; XP002420029, Beilstein Registry No. 2311871.
Database Beilstein [online] Beilstein Institut Zur Förderung Der Chemischen Wissenschaften; XP002420030, Beilstein Registry No. 8876646.
Database Beilstein [online] Beilstein Institut Zur Förderung Der Chemischen Wissenschaften; XP002420031, Beilstein Registry No. 2271400.
Database Beilstein [online] Beilstein Institut Zur Förderung Der Chemischen Wissenschaften; XP002420032, Beilstein Registry No. 2212095.
Database Beilstein [online] Beilstein Institut Zur Förderung Der Chemischen Wissenschaften; XP002420033, Beilstein Registry No. 8941955.
Database Beilstein [online] Beilstein Institut Zur Förderung Der Chemischen Wissenschaften; XP002420034, Database Accession No. 2312425.
Database Beilstein [online] Beilstein Institut Zur Förderung Der Chemischen Wissenschaften; XP002420035, Beilstein Registry No. 905950.
Database Beilstein [online] Beilstein Institut Zur Förderung Der Chemischen Wissenschaften; XP002420036, Beilstein Registry No. 2140308.
Database Beilstein [online] Beilstein Institut Zur Förderung Der Chemischen Wissenschaften; XP002420037, Beilstein Registry No. 134886.

(56) References Cited

OTHER PUBLICATIONS

Database Beilstein [online] Beilstein Institut Zur Förderung Der Chemischen Wissenschaften; XP002420038, Beilstein Registry No. 1961007.

Database CA [online] Chemical Abstracts Service, Columbus, Ohio, US, XP-002429584, Database Accession No. 81::153647, Organic Phosphate Stabilizers for Polyamides and Polyurethanes, abstract, Minagawa, M. (1974).

Database Caplus [online] Chemical Abstracts Service, Columbus, Ohio, US, XP-002387095, Database Accession No. 1981:572206, Effectiveness of Inhibitors in the Oxidation of Jet Fuel with an Initiator, abstract, Kovalev, et al.

Devassy, B.M., et al., "Zirconia Supported Phosphotungstic Acid as an Efficient Catalyst for Resorcinol *tert*-Butylation and *n*-Heptane Hydroisomerization," *J. Mol. Catalysis A: Chemical* 221:113-119 (2004).

Ding, et al., "Chemical Trapping Experiments Support a Cation-Radical Mechanism for the Oxidative Polymerization of Aniline," Journal of Polymer Science, Part A: Polymer Chemistry, vol. 37: 2569-2579 (1999).

Dordick, J.S., "Enzymatic Catalysis in Monophasic Organic Solvents," *Enzyme Microb. Technol.*, 11(4):194-211 (1989).

Dordick, J.S., et al., "Polymerization of Phenols Catalyzed by Peroxidase in Nonaqueous Media," *Biotechnology and Bioengineering*, 30(1):31-36 (1987).

English Abstract of Kovalev, G. I., et al., "Study of the Effectiveness of Inhibitors in Oxidation of Jet Fuel in a Closed Volume, "*Deposited Doc.*, VINITI: 443-82 (1981).

English Abstract of Kovalev, G.I., et al., "Effectiveness of Inhibitors in the Oxidation of Jet Fuel With an Initiator," *J. Neftekhimiya* (*Petroleum Chemistry*), 21(2): 287-298 (1981).

Faber, K., "Biotransformations in Organic Chemistry," A Textbook, Fourth Completely Revised and Extended Edition, Springer-Verlag pp. 347-349 (1953).

FS&T 821 "Antioxidant," [online], [retrieved on Oct. 29, 2002]. Retrieved from the Internet <URL: http://class.fst.ohio-state.edu/fst/lect/aa.pdf.

FS&T 821 "Food Lipids," [online], Oct. 2001 [retrieved on Oct. 29, 2002]. Retrieved from the Internet <URL: http://class.fst.ohio-state.edu/fst821/>.

FST 821 "Course Schedule," [online], [retrieved on Oct. 29, 2002]. Retrieved from the Internet <URL: http://class.fst.ohio-state.edu/fst821/>.

Hatayama, K., et al., "Anti-ulcer Effect of Isoprenyl Flavonoids. III.[1]) Synthesis and Anti-ulcer Activity of Metabolites of 2'-Carboxymethoxly-4,4'-bis(3-methyl-2-butenyloxy)chalcone[2])," *Chemical & Pharmaceutical Bulletin*, 33(4), 1327-1333(Apr. 1985).

Heidekum, A., et al., "Nafion/Silica Composite Material Reveals High Catalytic Potential in Acylation Reactions," *J. Catal.* 188:230-232 (1999).

Hidalgo, M.E., et al., "Antioxidant Activity of Depsides and Depsidones," Phytochemistry, 37(6):1585-1587 (1994).

Hofer, K., et al., "[[(Anilinooxalyl)amino]phenyl] Phosphite Stabilizers for Polypropylene," Chemical Abstracts Service, ZCAPLUS, document No. 77:62780 (1972).

http://www.machinerylubrication.com/Read/1 028/oxidation-lubricant (Mar. 29, 2010, pp. 1-7).

Ikeda, R., et al., "Novel Synthetic Pathway to a Poly(phenylene oxide). Laccase-Catalyzed Oxidative Polymerization of Syringic Acid," *Macromolecules*, 29:3053-3054 (1996).

International Preliminary Report on Patentability and Written Opinion for related foreign application PCT/US2005/025513, issued Jan. 23, 2007.

International Preliminary Report on Patentability for PCT/US2005/001946, issued Jul. 24, 2006; Title: Polymeric Antioxidants.

International Search Report for related foreign application PCT/US2007/015177, mailed on Jun. 13, 2008; Title: Novel Macromolecular Antioxidants Comprising Differing Antioxidant Moieties Structures Methods of Making and Using the Same.

International Search Report for related foreign application PCT/US2005/044021, mailed on May 22, 2006; Title: Process for the Synthesis of Polyalkylphenol Antioxidants.

International Search Report for related foreign application PCT/US2005/044022, mailed on May 2, 2006 Title: Synthesis of Sterically Hindered Phenol Based Macromolecular Antioxidants.

International Search Report for related foreign application PCT/US2005/044023, mailed on Nov. 3, 2006; Title: One Pot Process for Making Polymeric Antioxidants.

International Search Report for related foreign application PCT/US2005/044019, mailed on Apr. 28, 2006; Title: Synthesis of Aniline and Phenol-Based Macromonomers and Corresponding Polymers.

International Search Report for related foreign application PCT/US2005/025646, mailed on Mar. 13, 2006;Title: Photoacoustic Probe.

International Search Report for related foreign application PCT/US2005/025513, mailed on Mar. 13, 2006;Title: Anti-Oxidant Macromonomers and Polymers and Methods of Making and Using the Same.

International Search Report for related foreign application PCT/US2006/006355, mailed on Jul. 31, 2006; Title: Nitrogen and Hindered Phenol Containing Dual Functional Macromolecules: Synthesis and Their Antioxidant Performances in Organic Materials.

International Search Report for related foreign application PCT/US2006/010985, mailed on Dec. 19. 2006; Title: Alkylated Macromolecular Antioxidants and Methods of Making, and Using the Same.

International Search Report for related foreign application PCT/US2006/042240, mailed on May 3, 2007; Title: Macromolecular Antioxidants and Polymeric Macromolecular Antioxidants.

International Search Report for related foreign application PCT/US2006/042235, mailed on Apr. 27, 2007; Title: Macromolecular Antioxidants Based on Sterically Hindered Phenols and Phosphites.

International Search Report for related foreign application PCT/US2006/045929, mailed on Apr. 20, 2007; Title: Lubricant Oil Compositions.

Irgafos 126®, BASF publication, pp. 1-3, Jul. 2010.

Ismail, M.N. and Wazzan, A.A., "Evaluation of New Thermal Stabilizers and Antifatigue Agents for Rubber Vulcanizates," *Polymer-Plastics Tech. and Eng.*, 45:751-758 (2006).

Jayaprakasha, G.K., et al., "Antioxidant Activity of Grape Seed (*Vitis vinifera*) Extracts on Peroxidation Models in Vitro," *Food Chemistry*, 73:285-290 (2001).

Jialanella, G.and Pilrma, I., "Synthesis of Poly(vinyl alcohol-co-vinyl gallate) by the Chemical Modification of Poly(vinyl alcohol)," Polymer Bulletin 18:385-389 (1987).

Joossens, J., et al., "Diphenyl Phosphonate Inhibitors for the Urokinase-Type Plasminogen Activator: Optimization of the P4 Position," *J. Med. Chem.*, 49:5785-5793 (2006).

Kamitori, Y., et al., "Silica Gel as an Effective Catalyst for the Alkylation of Phenols and Some Heterocylic Aromatic Compounds," *J. Org. Chem.* 49: 4161-4165 (1984).

Kazandjian, R.Z., et al., "Enzymatic Analyses in Organic Solvents," *Biotechnology and Bioengineering*, XXVIII:417-421 (1986).

Khan, K.M., et al., "An Expedient Esterification of Aromatic Carboxylic Acids Using Sodium Bromate and Sodium Hydrogen Sulfite," *Tetrahedron* 59(29):5549-5554 (2003).

Kim, T. H., et al., "Melt Free-Radical Grafting of Hindered Phenol Antioxidant onto Polyethylene," *J. Applied Polymer Science*, 77:2968-2973 (2000).

Klibanov, A.M., et al., "Enzymatic Removal of Toxic Phenols and Anilines from Waste Waters," *J. of Applied Biochemistry*, 2(5):414-421 (1980).

Koshchii, V.A., et al. "Alkylation of Phenol by Alcohols in the Presence of Alumium Phenolate," *Org. Chem.* 24(7):1358-1361 (1988).

Lalancette, J.M., et al.,, "Metals Intercalated in Graphite. II. The Friedel-Crafts Reactions with $ALCL_3$-Graphite," *Can. J. Chem.* 52:589-591 (1974).

Li, et al., "Novel Multifunctional Polymers from Aromatic Diamines by Oxidative Polymerizations," Chemical Reviews, vol. 102(9): pp. 2925-2943 (2002).

(56) References Cited

OTHER PUBLICATIONS

Maki, M., et al., "Weather-Resistant Colored Polypropylene," Chemical Abstracts Service, ZCAPLUS, document No. 89:111364 (1978).

March, J., Advanced Organic Chemistry, McGraw Hill Book Company, New York, pp. 251-259 (1977).

Masada, H. and Oishi, Y., "A New Synthesis of aryl *t*-butyl Ethers," *Chem. Letters*, 57-58 (1978).

Masada, H. et al., "A New Heterogeneous Williamson Synthesis of Ethers Using *t*-alkyl Substrates," *The Chemical Society of Japan* 3:275-282 (1996).

Masada, H., et al., "A New Method for the Williamson Ether Synthesis Using *t*-alkyl Halides in Nonpolar Solvents," *The Chemical Society of Japan*, 2:164-166 (1995).

Mehdipour-Ataei, S., et al., "Novel Diols Containing Ester and Amide Groups and Resulting Poly(ester amide ester)s," *J. Applied Polymer Sci.*, 93:2699-2703 (2004), XP002420014.

Mejias, L., et al.,, "New Polymers From Natural Phenols Using Horseradish or Soybean Peroxidase," *Macromol. Biosci.*, 2:24-32 (2002).

Notification Concerning Transmittal of International Preliminary Report on Patentability for related foreign application PCT/US2007/015177, mailed on Jan. 15, 2009; Title: Novel Macromolecular Antioxidants Comprising Differing Antioxidant Moieties Structures Methods of Making and Using the Same.

Notification Concerning Transmittal of International Preliminary Report on Patentability for application PCT/US2006/042251, mailed on May 8, 2008; Title: Stabilized Polyolefin Composition.

Notification Concerning Transmittal of International Preliminary Report on Patentability for related foreign application PCT/US2005/025646, mailed on Dec. 20, 2006; Title: Photoacoustic Probe.

Notification Concerning Transmittal of International Search Report and Written Opinion of the International Searching Authority, or the Declaration for application PCT/US2006/042251, mailed on Feb. 22, 2007; Title: Stabilized Polyolefin Composition.

Notification of Transmittal of the International Search Report and the Written Opinion of the International Searching Authority, or the Declaration for related foreign application PCT/US2007/015177, mailed on Jun. 13, 2008; Title: Novel Macromolecular Antioxidants Comprising Differing Antioxidant Moieties Structures Methods of Making and Using the Same.

Ol'dekop, Yu. A., et al. "Simple Synthesis of the tert-butyl Ether of Phenol" Inst. Fiz-Org. Khim., Minsk, USSR. *Zhurnal Obshchei Khimii*, 50(2):475-6 (1980).

Overgaag, M., et al., "Rearrangement of Alkyl Phenyl Ethers Over Dealuminated HY Zeolites Under Liquid-Phase Conditions," *Applied Catalysis A: General, Elsevier Sci.*, 175(1-2):139-146 (1998).

Pätoprstý, V., et al., "$^{13}$ NMR Study of 3,9-Di(alkylphenoxy)-2,4,8,10-tetraoxa-3,9-diphosphaspiro[5.5]undecanes," *Magnetic Resonance in Chem*, 23(2):122-126 (1985).

Pirozhenko, V.V., et al., "NMR Study of Topomerization of N-Aroyl-*p*-Benzoquinonemonoimines," *Russian I. of Organic Chem.*, 31(11):1514-1519 (1995).

Quaschning, V., et al., "Properties of Modified Zirconia Used as Friedel-Crafts-Acylation Catalysts," *J. Catal.* 177:164-174 (1998).

RN 85650-63-1, 1984.

Ryu, K., et al., "Peroxidase-Catalyzed Polymerization of Phenols," Biocatalysis in Agricultural Biotechnology, Chapter10:141-157 (1988).

Sakthivel, A., et al., "Vapour Phase Tertiary Butylation of Phenol Over Sulfated Zirconia Catalyst," *Catal. Lett.*, 72(3-4):225-228 (2001).

Sartori G., et al., "Highly Selective Mono-*tert*-butylation of Aromatic Compounds," *Chem. Ind.*, (London), (22):762-763 (1985).

Scharpe, S.L., et al., "Serine Peptidase Modulators, Their Preparation, and Their Therapeutic Use," Chemical Abstracts Service, ZCAPLUS, document No. 131:223514 (1999).

Singh, A. and Kaplan, D. L., "Biocatalytic Route to Ascorbic Acid-Modified Polymers for Free-Radical Scavenging," *Adv. Matter.*, 15(15):1291-1294 (2003).

Spano, R., et al., "Substituted Anilides of 3-Monoethyl Ester of 4 Hydroxyisophthalic Acid," *J. of Med. Chem.*, 15(5):552-553.

Thompson, C. Ray, "Stability of Carotene in Alfalfa Meal: Effect of Antioxidants," *Industrial & Engineering Chemistry*, 24(5): 922-925 (1950).

Tsvetkov, O.N., et al,, "Alkylation of Phenols with Higher Olefins. Part I," *Int. Chem. Eng.* 7(1):104-121 (1967).

USPTO Search Report for U.S. Appl. No. 13/572,884, Mar. 20, 2013.

Written Opinion for related foreign application PCT/US2005/025646, mailed on Nov. 14, 2006; Title: Photoacoustic Probe.

XP-002419239, "Discover Our World of Effects for Polyolefins," *Ciba Speciality Chemicals*, (2003).

\* cited by examiner

FIG. 2 FT-IR spectrum of tris [N-(4-hydroxyphenyl),-3-(2,6-di-tert.-butyl, 4-hydroxyphenyl) propionamide] phosphite

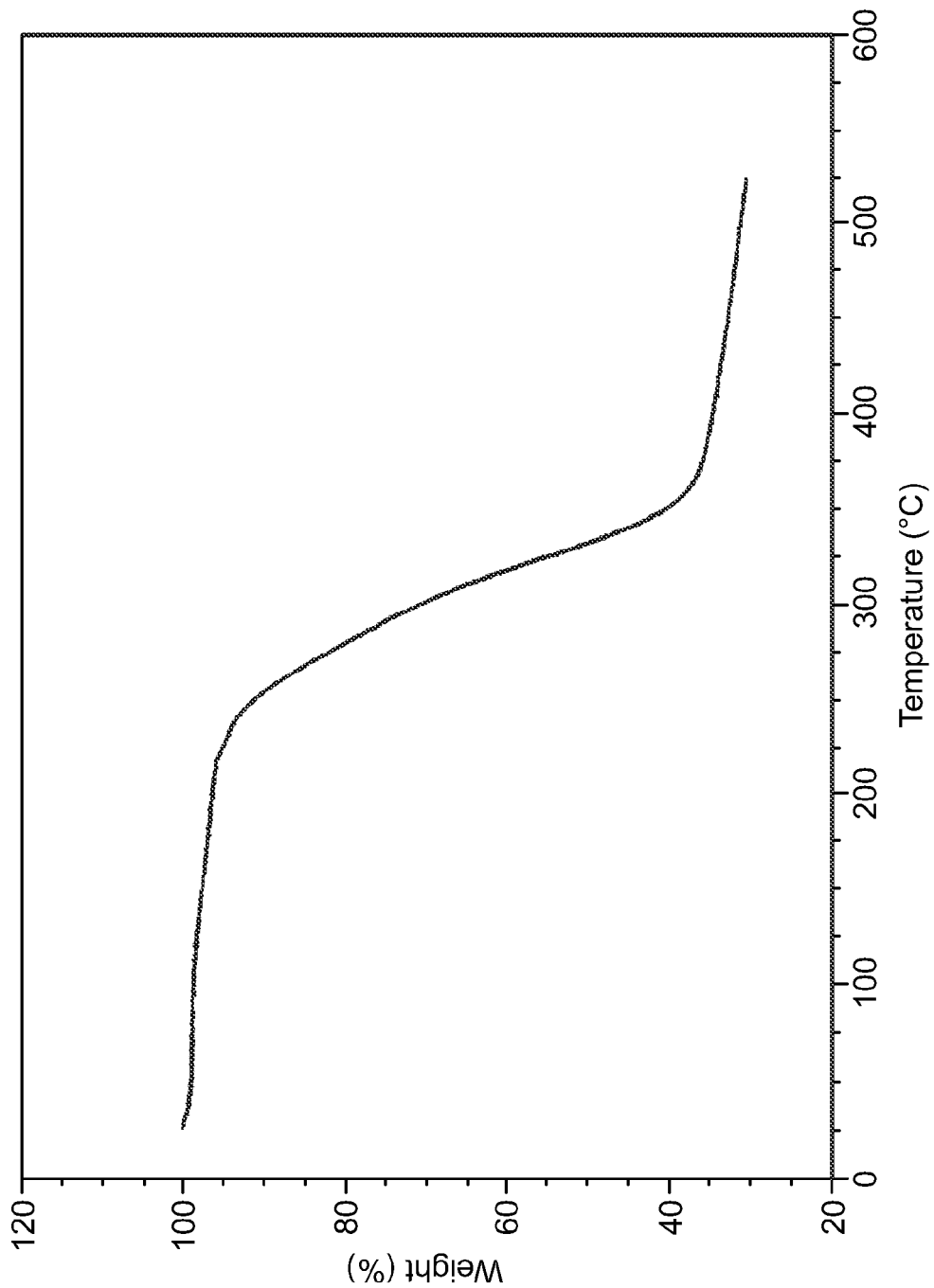
FIG. 4 TGA of tris [N-(4-hydroxyphenyl),-3-(2,6-di-tert.-butyl, 4-hydroxyphenyl) propionamide] phosphite

MACROMOLECULAR ANTIOXIDANTS BASED ON STERICALLY HINDERED PHENOLS AND PHOSPHITES

RELATED APPLICATIONS

This application is a continuation of U.S. application Ser. No. 13/572,884, filed Aug. 13, 2012, which is a continuation of U.S. application Ser. No. 13/109,800, filed May 17, 2011, which is a divisional of U.S. application Ser. No. 12/789,843, filed May 28, 2010, which is a continuation of U.S. application Ser. No. 11/293,844, filed Dec. 2, 2005, which claims the benefit of U.S. Provisional Application No. 60/633,196, filed on Dec. 3, 2004. The entire teachings of the above applications are incorporated herein by reference.

BACKGROUND OF THE INVENTION

Antioxidants are employed to prevent oxidation in a wide range of materials, for example, plastics, elastomers, lubricants, petroleum based products (lubricants, gasoline, aviation fuels, and engine oils), cooking oil, cosmetics, processed food products, and the like. While many small molecule antioxidants exist, there is a continuing need for new antioxidants that have improved properties.

The commercial use of triaryl phophites in latex is well known. Triaryl phophites containing alkyl-substituted phenyl rings have been found to be effective synthetic latex stabilizers. However, there is a continuing need for antioxidants with higher antioxidant activity and higher thermal stability.

SUMMARY OF THE INVENTION

The present invention relates to high performance, sterically hindered, phenol and phosphite based macromolecular antioxidants. In certain embodiments, the sterically hindered, phenol and phosphite based macromolecules of the present invention have enhanced antioxidant activity and better thermal stability compared to commercially available antioxidants.

In particular, the present invention pertains to sterically hindered phenol and phosphite based compounds represented by a formula selected from I-III:

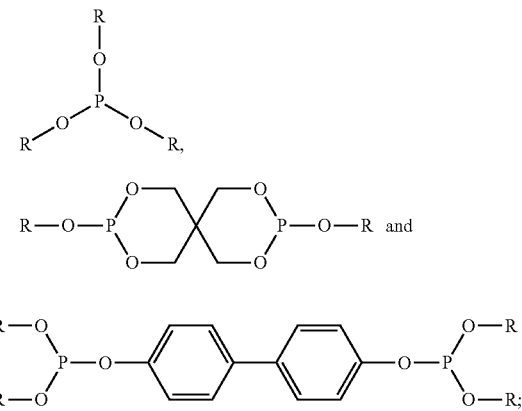

R is:

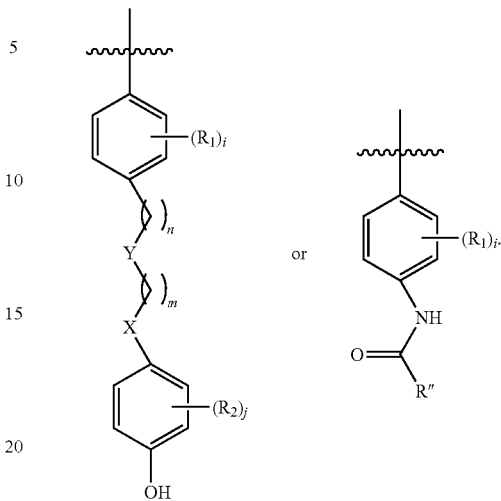

$R_1$ and $R_2$ in each occurrence, independently is an optionally substituted alkyl, an optionally substituted aryl or an optionally substituted aralkyl.

X and Y in each occurrence, independently is a bond, —O—, —NH—, —C(O)NH—, —NHC(O)—, —C(O)O—, —C(O)— or —CH$_2$—.

n and m in each occurrence, is independently 0 or a positive integer.

i and j in each occurrence, independently is 0, 1, 2, 3 or 4.

R" is an optionally substituted alkyl.

In another embodiment, the present invention pertains to methods of preventing oxidation. The method comprises combining an oxidizable material with a compound represented by a structural formula selected from I-III.

In yet another embodiment, the present invention pertains to methods for preparing sterically hindered phenol and phosphite based compound, having a formula selected from I-III. The method comprises combining a phenol containing compound with a phosphorous containing compound, such as, phosphorous trichloride in a suitable solvent under conditions suitable for reaction of the phenol containing compound with the phosphorous containing compound.

In yet another embodiment the present invention pertains to the use of the disclosed compounds as antioxidants in a wide range of materials including, but not limited to, food, plastics, elastomers, composites and petroleum based products.

The compounds of the invention provide significant oxidative resistance and thermal stability. The compounds of the invention generally have higher oxidative induction time, higher thermal stability and lower change of Melt flow or viscosity than commercially available antioxidants. Without wishing to be bound by theory it is believed that the enhanced molecular activity comes from the synergistic chemistry between the two main integral components (phenolic and phosphite components) of these macromolecular antioxidants.

In certain embodiments, the compounds disclosed herein, do not discolor the substance to which they are added. In certain other embodiments the compounds disclosed herein impart fewer odors to the substance to which they are added than currently available antioxidants. In certain other embodiments, the disclosed compounds provide enhanced oven aging properties to organic materials subject to attack by heat and oxygen. In certain other embodiments the disclosed compounds have higher antioxidant activity and higher thermal stability than antioxidants which are currently known or used in the art.

BRIEF DESCRIPTION OF THE DRAWINGS

FIG. 4 is the Thermogravimetric Analysis (TGA) of tris[N-(4-hydroxyphenyl),-3-(2,6-di-tert.-butyl, 4-hydroxyphenyl) propionamide]phosphate of the invention, obtained using a 2950 TGA HR V5 4A and a Universal V3.8B TA with a sample size of 7.7400 mg by a Ramp method.

DETAILED DESCRIPTION OF THE INVENTION

Figure 1:
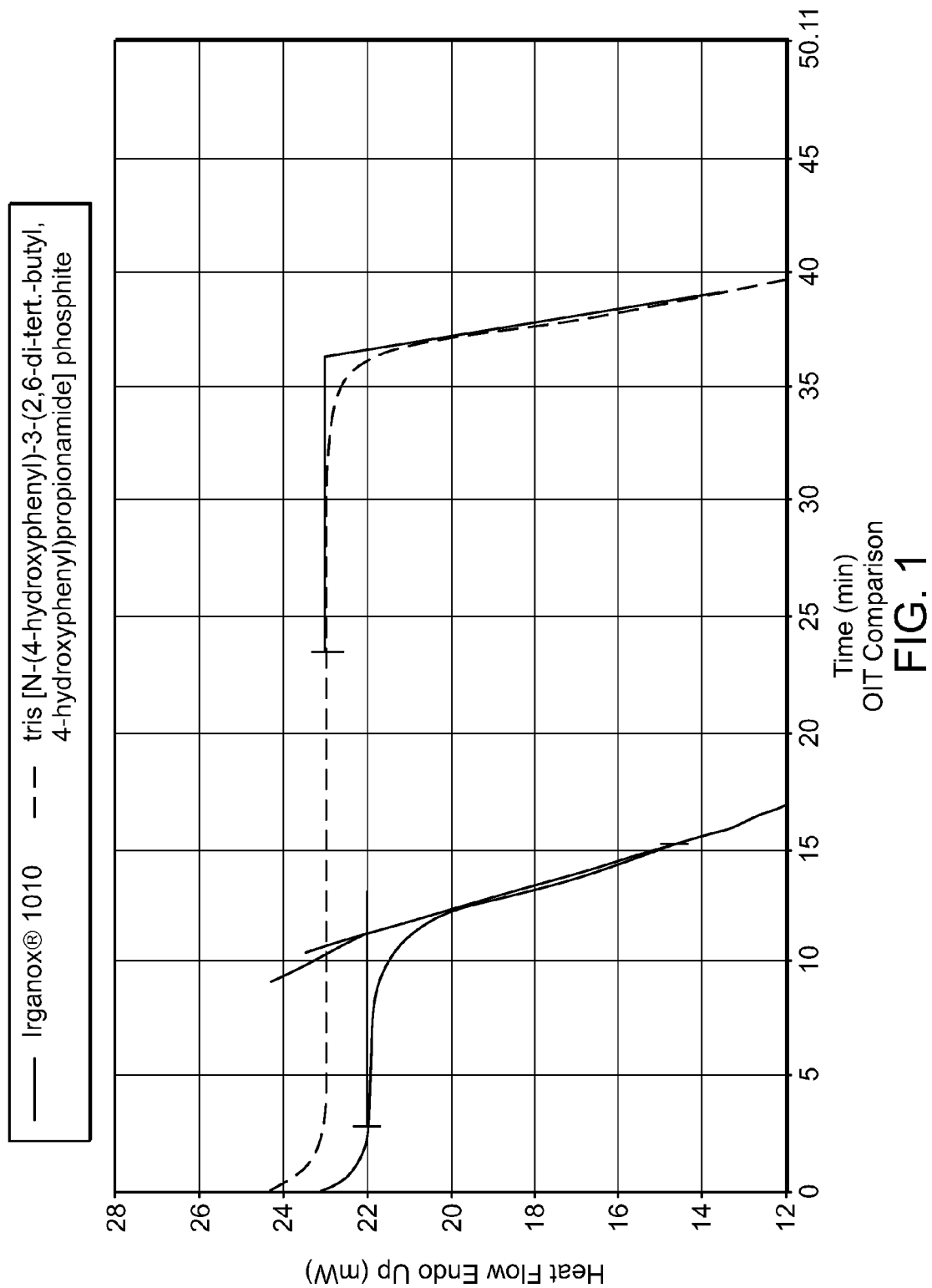
FIG. 1, is a comparison of the Oxidative Induction Time (OIT) of one embodiment of the invention, namely, tris[N-(4-hydroxyphenyl),-3-(2,6-di-tert.-butyl, 4-hydroxyphenyl) propionamide]phosphate, versus commercially available Irganox® 1010 in polypropylene (PP) at 1000 ppm (extruded at 230° C.).
Figure 2:
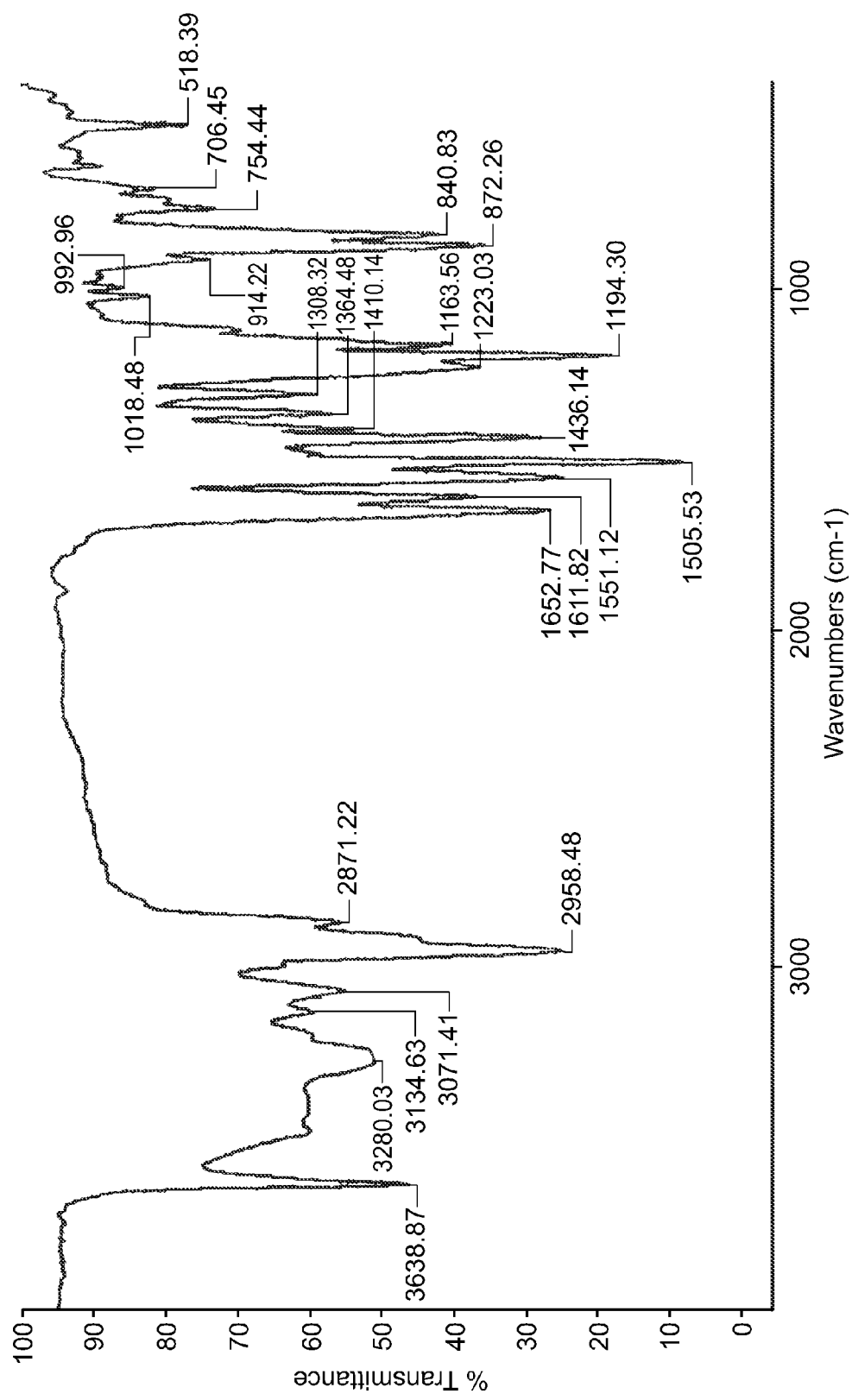
FIG. 2 is the Fourier Transform Infrared (FT-IR) spectrum of tris[N-(4-hydroxyphenyl),-3-(2,6-di-tert.-butyl, 4-hydroxyphenyl)propionamide]phosphate of the invention.
Figure 3:
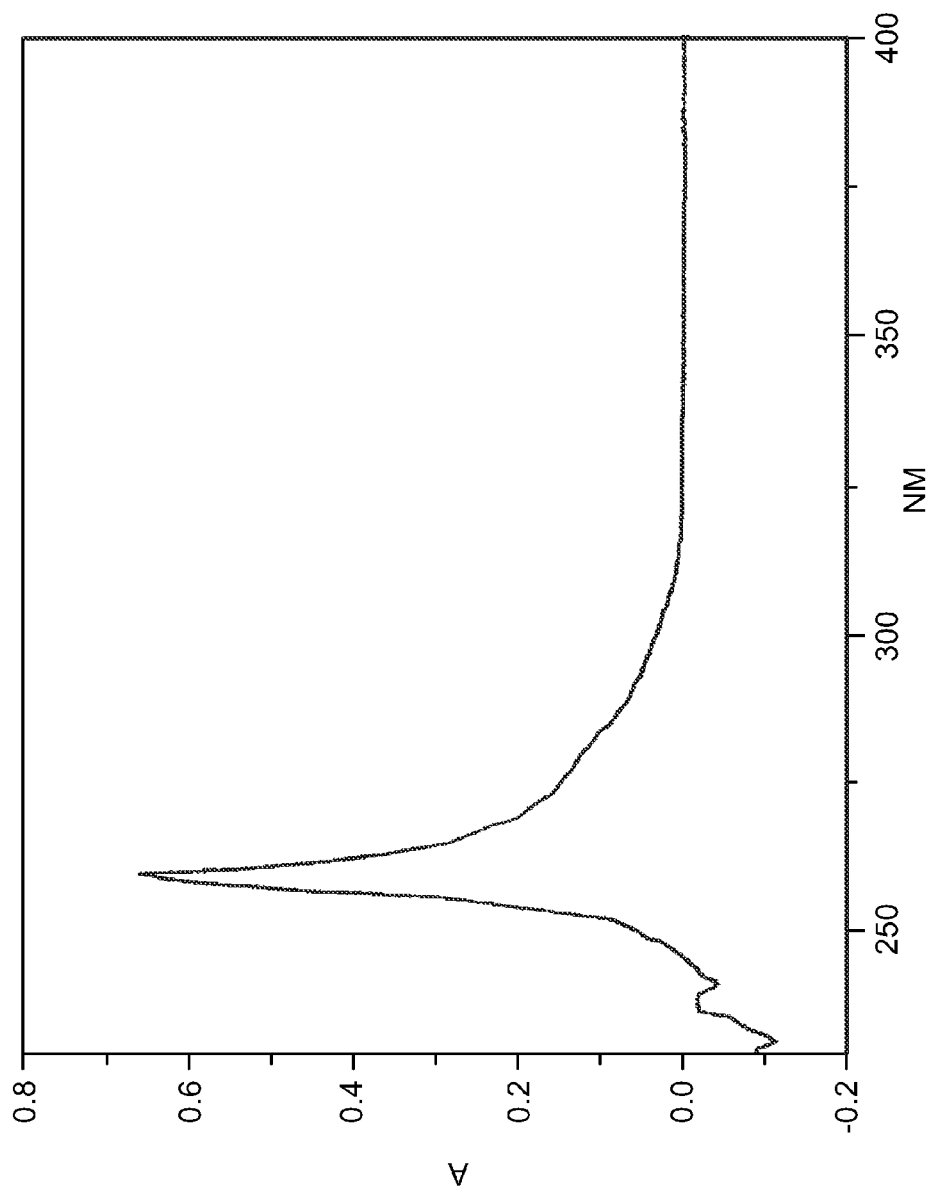
FIG. 3 is the Ultraviolet (UV) spectrum of tris[N-(4-hydroxyphenyl),-3-(2,6-di-tert.-butyl, 4-hydroxyphenyl)propionamide]phosphate of the invention.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

In one embodiment, the present invention pertains to sterically hindered phenol and phosphite based compounds, represented by a formula selected from I-III:

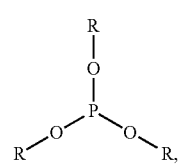

I

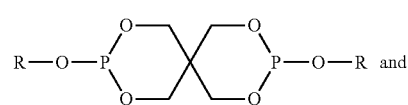

II

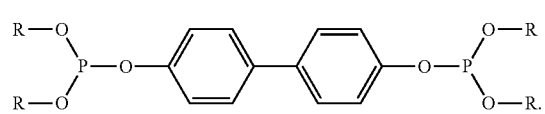

III

R is:

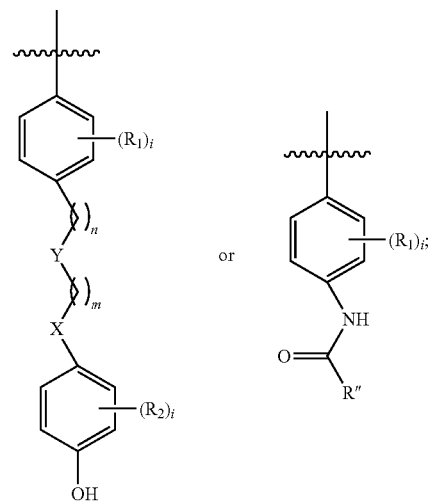

$R_1$ and $R_2$ in each occurrence, independently is an optionally substituted alkyl, optionally substituted aryl or optionally substituted aralkyl. In one embodiment, each $R_1$ and $R_2$ are independently an optionally substituted alkyl. In another embodiment, each $R_1$ and $R_2$ are independently a C1-C6 alkyl.

In one embodiment R is:

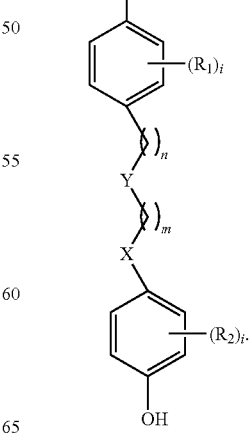

In another embodiment R is:

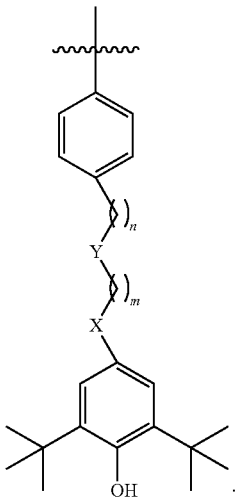

In yet another embodiment R is:

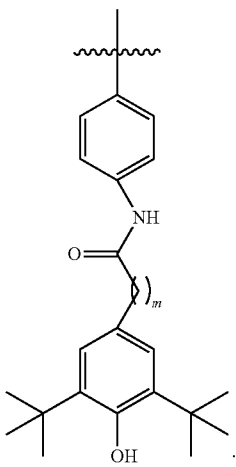

X and Y in each occurrence independently is a bond, —O—, —NH—, —C(O)NH—, —NHC(O)—, —C(O)O—, —OC(O)— or —CH₂—. In one embodiment, X and Y in each occurrence independently is a bond or —CH₂—. In another embodiment, X and Y in each occurrence independently is a bond, —O— or —CH₂—. In yet another embodiment, X and Y in each occurrence independently is a bond, —NH— or —CH₂—. In yet another embodiment, X and Y in each occurrence independently is a bond, —C(O)NH— or —CH₂—. In yet another embodiment, X and Y in each occurrence independently is a bond, —NHC(O)—, or —CH₂—. In yet another embodiment, X and Y in each occurrence independently is a bond, —C(O)O— or —CH₂—. In yet another embodiment, X and Y in each occurrence independently is a bond, —OC(O)— or —CH₂—.

n and m in each occurrence independently is 0 or a positive integer. In one embodiment, n and m in each occurrence independently is 0 to 18. In another embodiment, n and m in each occurrence independently is 0 to 12. In yet another embodiment, n and m are in each occurrence independently is 0 to 6.

i and j in each occurrence independently is 0, 1, 2, 3 or 4. In one embodiment i and j in each occurrence independently is 0, 1 or 2. In a particular embodiment, i is 0. In another particular embodiment j is 2.

R″ is an optionally substituted alkyl. In one embodiment R″ is C1-C6 alkyl.

In one embodiment the present invention pertains to compounds represented by structural formula I.

In one embodiment the present invention pertains to compounds represented by structural formula II.

In one embodiment the present invention pertains to compounds represented by structural formula III.

In a particular embodiment, for compounds of the present invention represented by structural formulas I-III, R is:

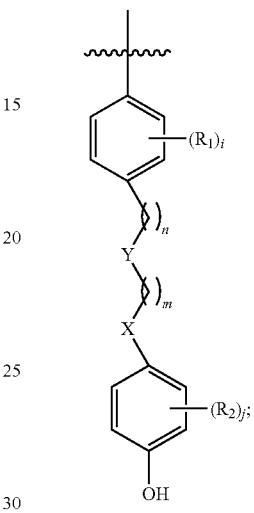

and n and m in each occurrence independently is 0 to 12, and the remainder of the variables are as described above for structural formulas I-III.

In another particular embodiment, for compounds of the present invention represented by structural formulas I-III, R, n and m are as described immediately above, and R₁ and R₂ in each occurrence, independently is an optionally substituted alkyl; i and j in each occurrence independently is 0, 1 or 2; and the remainder of the variables are as described above for structural formulas I-III.

In yet another particular embodiment, for compounds of the present invention represented by structural formulas I-III, R₁, R₂, i and j are as described immediately above, and R is:

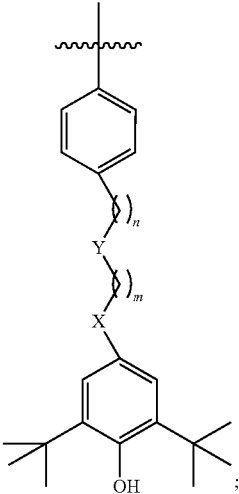

n and m in each occurrence, independently is 0 to 6; and the remainder of the variables are as described above for structural formulas I-III.

In another particular embodiment, for compounds of the present invention represented by structural formulas I-III, $R_1$, $R_2$, i, j, R, n and m are as described immediately above, and X and Y in each occurrence, independently is a bond or —$CH_2$—; and the remainder of the variables are as described above for structural formulas I-III.

In another particular embodiment, for compounds of the present invention represented by structural formulas I-III, $R_1$, $R_2$, i, j, R, n and m are as described immediately above, and X and Y in each occurrence, independently is a bond, —O— or —$CH_2$—; and the remainder of the variables are as described above for structural formulas I-III.

In another particular embodiment, for compounds of the present invention represented by structural formulas I-III, $R_1$, $R_2$, i, j, R, n and m are as described immediately above, and X and Y in each occurrence, independently is a bond, —NH— or —$CH_2$—; and the remainder of the variables are as described above for structural formulas I-III.

In another particular embodiment, for compounds of the present invention represented by structural formulas I-III, $R_1$, $R_2$, i, j, R, n and m are as described immediately above, and X and Y in each occurrence, independently is a bond, —C(O)NH— or —$CH_2$—; and the remainder of the variables are as described above for structural formulas I-III.

In another particular embodiment, for compounds of the present invention represented by structural formulas I-III, $R_1$, $R_2$, i, j, R, n and m are as described immediately above, and X and Y in each occurrence, independently is a bond, —NHC(O)—, or —$CH_2$—; and the remainder of the variables are as described above for structural formulas I-III.

In another particular embodiment, for compounds of the present invention represented by structural formulas I-III, $R_1$, $R_2$, i, j, R, n and m are as described immediately above, and X and Y in each occurrence, independently is a bond, —C(O)O— or —$CH_2$—; and the remainder of the variables are as described above for structural formulas I-III.

In another particular embodiment, for compounds of the present invention represented by structural formulas I-III, $R_1$, $R_2$, i, j, R, n and m are as described immediately above, and X and Y in each occurrence, independently is a bond, —OC(O)— or —$CH_2$—; and the remainder of the variables are as described above for structural formulas I-III.

In an additional embodiment, for formulas I-III R is:

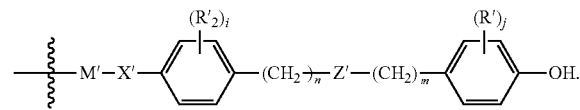

n and m in each occurrence, independently is 0 or a positive integer. In one embodiment, n and m in each occurrence, independently is 0 to 18. In another embodiment, n and m in each occurrence, independently is 0 to 12. In yet another embodiment, n and m in each occurrence, independently is 0 to 6.

i and j in each occurrence, independently is 0, 1, 2, 3 or 4. In one embodiment, i and j in each occurrence, independently is 0, 1 or 2. In a particular embodiment, i is 0. In another particular embodiment, j is 2.

Z' is —C(O)O—, —OC(O)—, —C(O)NH—, —NHC(O)—, —NH—, —CH=N—, —C(O)—, —O—, —S—, —C(O)OC(O)— or a bond. In one embodiment, Z' is —C(O)O—. In another embodiment, Z' is —OC(O)—. In yet another embodiment, Z' is —C(O)NH—. In yet another embodiment, Z' is —NHC(O)—. In yet another embodiment, Z' is —NH—. In yet another embodiment, Z' is —CH=N—. In yet another embodiment, Z' is —C(O)—. In yet another embodiment, Z' is —O—. In yet another embodiment, Z' is —S—. In yet another embodiment, Z' is —C(O)OC(O)—. In yet another embodiment, Z' is a bond.

R' is an optionally substituted C1-C6 alkyl, —OH, —$NH_2$, —SH, an optionally substituted aryl, an ester or

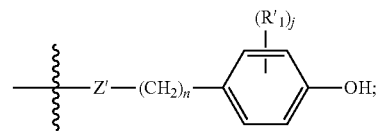

wherein at least one R' adjacent to the —OH group is an optionally substituted bulky alkyl group (e.g., butyl, sec-butyl, tert-butyl, 2-propyl, 1,1-dimethylhexyl, and the like).

$R'_1$ is an optionally substituted C1-C6 alkyl, an optionally substituted aryl, an optionally substituted aralkyl, —OH, —$NH_2$, —SH, or C1-C6 alkyl ester wherein at least one $R_1$ adjacent to the —OH group is a bulky alkyl group (e.g., butyl, sec-butyl, tert-butyl, 2-propyl, 1,1-dimethylhexyl, and the like).).

$R'_2$ is an optionally substituted C1-C6 alkyl, an optionally substituted aryl, an optionally substituted aralkyl, —OH, —$NH_2$, —SH, or ester.

X' is —C(O)O—, —OC(O)—, —C(O)NH—, —NHC(O)—, —NH—, —CH=N—, —C(O)—, —O—, —S—, —C(O)OC(O)— or a bond. In one embodiment X' is —C(O)O—. In another embodiment X' is —OC(O)—. In yet another embodiment X' is —C(O)NH—. In yet another embodiment X' is —NHC(O)—. In yet another embodiment X' is —NH—. In yet another embodiment X' is —CH=N—. In yet another embodiment X' is —C(O)—. In yet another embodiment X' is —O—. In yet another embodiment X' is —S—. In yet another embodiment X' is —C(O)OC(O)—. In yet another embodiment X' is a bond.

M' is H, an optionally substituted aryl, an optionally substituted C1-C20 linear or branched alkyl chain with or without any functional group anywhere in the chain, or

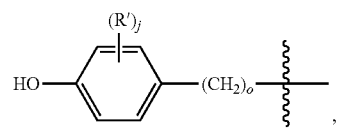

o is 0 or a positive integer. Preferably o is 0 to 18. More preferably o is 0 to 12. Even more preferably o is 0 to 6.

In yet another embodiment, for formulas I-III R is:

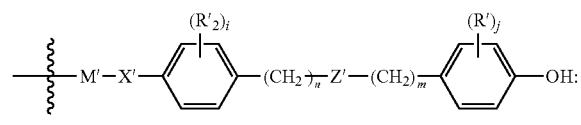

R'$_2$ is C1-C6 alkyl, —OH, —NH$_2$, —SH, aryl, ester, aralkyl or

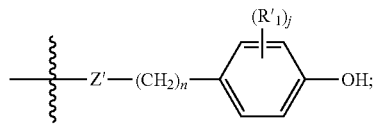

wherein at least one R'$_2$ is —OH, and the values and preferred values for the remainder of the variables for R are as described immediately above.

In yet another embodiment, the present invention relates to a compound of formula I-III, wherein M is

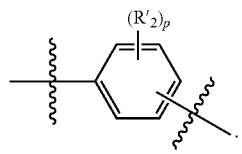

Wherein p is 0, 1, 2, 3 or 4; and the values and preferred values for the remainder of the variables are as described above for formulas I-III.

The term "alkyl" as used herein means a saturated straight-chain, branched or cyclic hydrocarbon. When straight-chained or branched, an alkyl group is typically C1-C8, more typically C1-C6; when cyclic, an alkyl group is typically C3-C12, more typically C3-C7 alkyl ester. Examples of alkyl groups include methyl, ethyl, n-propyl, iso-propyl, n-butyl, sec-butyl and tent-butyl and 1,1-dimethylhexyl.

The term "alkoxy" as used herein is represented by —OR, wherein R is an alkyl group as defined above.

The term "acyl" as used herein is represented by —C(O)R, wherein R is an alkyl group as defined above.

The term "alkyl ester" as used herein means a group represented by —C(O)OR, where R is an alkyl group as defined above.

The term "aromatic group" used alone or as part of a larger moiety as in "aralkyl", includes carbocyclic aromatic rings and heteroaryl rings. The term "aromatic group" may be used interchangeably with the terms "aryl", "aryl ring" "aromatic ring", "aryl group" and "aromatic group".

Carbocyclic aromatic ring groups have only carbon ring atoms (typically six to fourteen) and include monocyclic aromatic rings such as phenyl and fused polycyclic aromatic ring systems in which two or more carbocyclic aromatic rings are fused to one another. Examples include 1-naphthyl, 2-naphthyl, 1-anthracyl and 2-anthracyl. Also included within the scope of the term "carbocyclic aromatic ring", as it is used herein, is a group in which an aromatic ring is fused to one or more non-aromatic rings (carbocyclic or heterocyclic), such as in an indanyl, phthalimidyl, naphthimidyl, phenanthridinyl, or tetrahydronaphthyl, where the radical or point of attachment is on the aromatic ring.

The term "heteroaryl", "heteroaromatic", "heteroaryl ring", "heteroaryl group" and "heteroaromatic group", used alone or as part of a larger moiety as in "heteroaralkyl" refers to heteroaromatic ring groups having five to fourteen members, including monocyclic heteroaromatic rings and polycyclic aromatic rings in which a monocyclic aromatic ring is fused to one or more other aromatic ring. Heteroaryl groups have one or more ring heteroatoms. Examples of heteroaryl groups include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 3-pyrazolyl, 4-pyrazolyl, 1-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, 3-quinolinyl, 1-isoindolyl and 3-isoindolyl. Also included within the scope of the term "heteroaryl", as it is used herein, is a group in which an aromatic ring is fused to one or more non-aromatic rings (carbocyclic or heterocyclic), where the radical or point of attachment is on the aromatic ring.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heteroaryl or non-aromatic heterocyclic group. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR" (as in N-substituted pyrrolidinyl), wherein R" is a suitable substituent for the nitrogen atom in the ring of a non-aromatic nitrogen-containing heterocyclic group, as defined below.

An "aralkyl group", as used herein is an alkyl groups substituted with an aryl group as defined above.

An optionally substituted aryl group as defined herein may contain one or more substitutable ring atoms, such as carbon or nitrogen ring atoms. Examples of suitable substituents on a substitutable ring carbon atom of an aryl group include —OH, C1-C3 alkyl, C1-C3 haloalkyl, —NO$_2$, C1-C3 alkoxy, C1-C3 haloalkoxy, —CN, —NH$_2$, C1-C3 alkylamino, C1-C3 dialkylamino, —C(O)NH$_2$, —C(O)NH(C1-C3 alkyl), —C(O)(C1-C3 alkyl), —NHC(O)H, —NHC(O)(C1-C3 alkyl), —C(O)N(C1-C3 alkyl)$_2$, —NHC(O)O—(C1-C3 alkyl), —C(O)OH, —C(O)O—(C1-C3 alkyl), —NHC(O)NH$_2$, —NHC(O)NH(C1-C3 alkyl), —NHC(O)N(C1-C3 alkyl)$_2$, —SO$_2$NH$_2$—SO$_2$NH(C1-C3alkyl), —SO$_2$N(C1-C3alkyl)$_2$, NHSO$_2$H or NHSO$_2$(C1-C3 alkyl). Preferred substituents on aryl groups are as defined throughout the specification. In certain embodiments optionally substituted aryl groups are unsubstituted Examples of suitable substituents on a substitutable ring nitrogen atom of an aryl group include C1-C3 alkyl, NH$_2$, C1-C3 alkylamino, C1-C3 dialkylamino, —C(O)NH$_2$, —C(O)NH(C1-C3 alkyl), —C(O)(C1-C3 alkyl), —CO$_2$R, —C(O)C(O)R, —C(O)CH$_3$, —C(O)OH, —C(O)O—(C1-C3 alkyl), —SO$_2$NH$_2$—SO$_2$NH(C1-C3alkyl), —SO$_2$N(C1-C3alkyl)$_2$, NHSO$_2$H, NHSO$_2$(C1-C3 alkyl), —C(=S)NH$_2$, —C(=S)NH(C1-C3 alkyl), —C(=S)N(C1-C3 alkyl)$_2$, —C(=NH)—N(H)$_2$, —C(=NH)—NH(C1-C3 alkyl) and —C(=NH)—N(C1-C3 alkyl)$_2$, An optionally substituted alkyl group as defined herein may contain one or more substituents. Examples of suitable substituents for an alkyl group include those listed above for a substitutable carbon of an aryl and the following: =O, =S, =NNHR, =NN(R)$_2$, =NNHC(O)R, =NNHCO$_2$(alkyl), =NNHSO$_2$(alkyl), =NR, spiro cycloalkyl group or fused cycloalkyl group. R** in each occurrence, independently is —H or C1-C6 alkyl. Preferred substituents on alkyl groups are as defined throughout the specification. In certain embodiments optionally substituted alkyl groups are unsubstituted.

A "spiro cycloalkyl" group is a cycloalkyl group which shares one ring carbon atom with a carbon atom in an alkylene group or alkyl group, wherein the carbon atom being shared in the alkyl group is not a terminal carbon atom.

Without wishing to be bound by any theory or limited to any mechanism it is believed that macromolecular antioxidants of the present invention exploit the differences in activities (ks, equilibrium constant) of, for example, homo- or hetero-type antioxidant moieties. Antioxidant moieties include, for example, hindered phenolic groups, unhindered phenolic groups, aminic groups and thioester groups, etc. of which there can be one or more present in each macromolecular antioxidant molecule. As used herein a homo-type antioxidant macromolecule comprises antioxidant moieties which are all same, for example, hindered phenolic, —OH groups. As used herein a hetero-type antioxidant macromolecule comprises at least one different type of moiety, for example, hindred phenolic and aminic groups in the one macromolecule.

This difference in activities can be the result of, for example, the substitutions on neighboring carbons or the local chemical or physical environment (for example, due to electrochemical or stereochemical factors) which can be due in part to the macromolecular nature of molecules.

In one embodiment of the present invention, a series of macromolecular antioxidant moieties of the present invention with different chemical structures can be represented by W1H, W2H, W3H, . . . to WnH. In one embodiment of the present invention, two types of antioxidant moieties of the present invention can be represented by: W1H and W2H. In certain embodiments W1H and W2H can have rate constants of k1 and k2 respectively. The reactions involving these moieties and peroxyl radicals can be represented as:

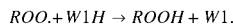 (1)

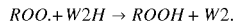 (2)

where ROO. is a peroxyl radical resulting from, for example, initiation steps involving oxidation activity, for example:

RH→R.+H.     (3)

R.+O2→ROO.     (4)

In one particular embodiment of the present invention k1>>k2 in equations (1) and (2). As a result, the reactions would take place in such a way that there is a decrease in concentration of W1. free radicals due their participation in the regeneration of active moiety W2H in the molecule according equation (5):

W1.+W2H→W1H+W2.     (5) (transfer equilibrium)

This transfer mechanism may take place either in intra- or inter-molecular macromolecules. The transfer mechanism (5) could take place between moieties residing on the same macromolecule (intra-type) or residing on different macromolecules (inter-type).

In certain embodiments of the present invention, the antioxidant properties described immediately above (equation 5) of the macromolecular antioxidants of the present invention result in advantages including, but not limited to:

a) Consumption of free radicals W1. according to equation (5) can result in a decrease of reactions of W1. with hydroperoxides and hydrocarbons (RH).
b) The regeneration of W1H provides extended protection of materials. This is a generous benefit to sacrificial type of antioxidants that are used today. Regeneration of W1H assists in combating the oxidation process. The increase in the concentration of antioxidant moieties W1H (according to equation 5) extends the shelf life of materials.

In certain embodiments of the present invention, the following items are of significant interest for enhanced antioxidant activity in the design of the macromolecular antioxidants of the present invention:

a) The activity of proposed macromolecular antioxidant is dependent on the regeneration of W1H in equation (5) either through inter- or intra-molecular activities involving homo- or hetero-type antioxidant moieties.
b) Depending on the rates constants of W1H and W2H it is possible to achieve performance enhancements by many multiples and not just incremental improvements.

In certain embodiments of the present invention, more than two types of antioxidant moieties with different rate constants are used in the methods of the present invention.

In certain embodiments, the present invention pertains to the use of the disclosed compounds to inhibit oxidation in an oxidizable material.

For purposes of the present invention, a method of "inhibiting oxidation" is a method that inhibits the propagation of a free radical-mediated process. Free radicals can be generated by heat, light, ionizing radiation, metal ions and some proteins and enzymes. Inhibiting oxidation also includes inhibiting reactions caused by the presence of oxygen, ozone or another compound capable of generating these gases or reactive equivalents of these gases.

As used herein the term "oxidizable material" is any material which is subject to oxidation by free-radicals or oxidative reaction caused by the presence of oxygen, ozone or another compound capable of generating these gases or reactive equivalents thereof.

Antioxidant compounds of the present invention can be used to prevent oxidation in a wide variety of compositions where free radical mediated oxidation leads to deterioration of the quality of the composition, including edible products such as oils, foods (e.g., meat products, dairy products, cereals, etc.), and other products containing fats or other compounds subject to oxidation. Antioxidant compounds can also be present in plastics and other polymers, elastomers (e.g., natural or synthetic rubber), petroleum products (e.g., fossil fuels such as gasoline, kerosene, diesel oil, heating oil, propane, jet fuel), lubricants, paints, pigments or other colored items, soaps and cosmetics (e.g., creams, lotions, hair products). The antioxidant compounds can be used to coat a metal as a rust and corrosion inhibitor. Antioxidant compounds additionally can protect antioxidant vitamins (Vitamin A, Vitamin C, Vitamin E) and pharmaceutical products from degradation. In food products, the antioxidant compounds can prevent rancidity. In plastics, the antioxidant compounds can prevent the plastic from becoming brittle and cracking.

Antioxidant compounds of the present invention can be added to oils to prolong their shelf life and properties. These oils can be formulated as vegetable shortening or margarine. Oils generally come from plant sources and include cottonseed oil, linseed oil, olive oil, palm oil, corn oil, peanut oil, soybean oil, castor oil, coconut oil, safflower oil, sunflower oil, canola (rapeseed) oil and sesame oil. These oils contain one or more unsaturated fatty acids such as caproleic acid, palmitoleic acid, oleic acid, vaccenic acid, elaidic acid, brassidic acid, erucic acid, nervonic acid, linoleic acid, eleosteric acid, alpha-linolenic acid, gamma-linolenic acid, and arachidonic acid, or partially hydrogenated or trans-hydrogenated variants thereof. Antioxidant compounds of the present invention are also advantageously added to food or other consumable products containing one or more of these fatty acids.

The shelf life of many materials and substances contained within the materials, such as packaging materials, are enhanced by the presence of an antioxidant compound of the present invention. The addition of an antioxidant compound to a packaging material is believed to provide additional protection to the product contained inside the package. In addition, the properties of many packaging materials themselves, particularly polymers, are enhanced by the presence of an antioxidant regardless of the application (i.e., not limited to use in packaging). Common examples of packaging materials include paper, cardboard and various plastics and polymers. A packaging material can be coated with an antioxidant compound (e.g., by spraying the antioxidant compound or by applying as a thin film coating), blended with or mixed with an antioxidant compound, or otherwise have an antioxidant compound present within it.

The entire teachings of each of the following applications are incorporated herein by reference:
Provisional Patent Application No. 60/632,893, filed Dec. 3, 2004, Title: Process For The Synthesis Of Polyalkylphenol Antioxidants, by Suizhou Yang, et al;
Provisional Patent Application No. 60/633,197, filed Dec. 3, 2004, Title: Synthesis Of Sterically Hindered Phenol Based Macromolecular Antioxidants, by Ashish Dhawan, et al.;
Provisional Patent Application No. 60/633,252, filed Dec. 3, 2004, Title: One Pot Process For Making Polymeric Antioxidants, by Vijayendra Kumar, et al.;
Provisional Patent Application No. 60/633,196, filed Dec. 3, 2004, Title: Synthesis Of Aniline And Phenol-Based Macromonomers And Corresponding Polymers, by Rajesh Kumar, et al.;
patent application Ser. No. 11/184,724, filed Jul. 19, 2005 (U.S. Patent Publication No. 2006/0041094 published Feb. 23, 2006), Title: Anti-Oxidant Macromonomers And Polymers And Methods Of Making And Using The Same, by Ashok L. Cholli;
patent application Ser. No. 11/184,716 filed Jul. 19, 2005 (U.S. Patent Publication No. 2006/0041087 published Feb. 23, 2006), Title: Anti-Oxidant Macromonomers And Polymers And Methods Of Making And Using The Same, by Ashok L. Cholli;
Provisional Patent Application No. 60/655,169, filed Feb. 22, 2005, Title: Nitrogen And Hindered Phenol Containing Dual Functional Macromolecules: Synthesis And Their Antioxidant Performances In Organic Materials, by Rajesh Kumar, et al.
Provisional Patent Application No. 60/655,169, filed Mar. 25, 2005, Title: Alkylated Macromolecular Antioxidants And Methods Of Making, And Using The Same, by Rajesh Kumar, et al.
Provisional Patent Application No. 60/731,125, filed Oct. 27, 2005, Title: Macromolecular Antioxidants And Polymeric Macromolecular Antioxidants, by Ashok L. Cholli, et al.
patent application Ser. No. 11/040,193, filed Jan. 21, 2005 (U.S. Pat. No. 7,323,511 issued Jan. 29, 2008), Title: Post-Coupling Synthetic Approach For Polymeric Antioxidants, by Ashok L. Choll, et al.;
Patent Application No.: PCT/US2005/001948, filed Jan. 21, 2005 (WO 2005/070974 published Aug. 4, 2005), Title: Post-Coupling Synthetic Approach For Polymeric Antioxidants, by Ashok L. Cholli et al.;
Patent Application No.: PCT/US2005/001946, filed Jan. 21, 2005 (WO 2005/071005 published Aug. 4, 2005), Title: Polymeric Antioxidants, by Ashok L. Choll, et al.;
Patent Application No.: PCT/US03/10782, filed Apr. 4, 2003 (WO 2003/087260 published Oct. 23, 2003), Title: Polymeric Antioxidants, by Ashok L. Choll, et al.;
patent application Ser. No. 10/761,933, filed Jan. 21, 2004 (U.S. Pat. No. 7,595,074 issued Sep. 29, 2009), Title: Polymeric Antioxidants, by Ashish Dhawan, et al.;
patent application Ser. No. 10/408,679, filed Apr. 4, 2003 (U.S. Pat. No. 7,223,432 issued May 29, 2007), Title: Polymeric Antioxidants, by Ashok L. Choll, et al.;

In another particular embodiment, the present invention relates to a process for preparing compounds of the present invention. Compounds of the present invention can be prepared by a one pot process, comprising the step of combining a phenol containing compound with a suitable phosphorous containing compound in a suitable solvent under conditions suitable for the reaction of the phenol containing compound with the phosphorous containing compound.

Suitable phenol containing compounds include:

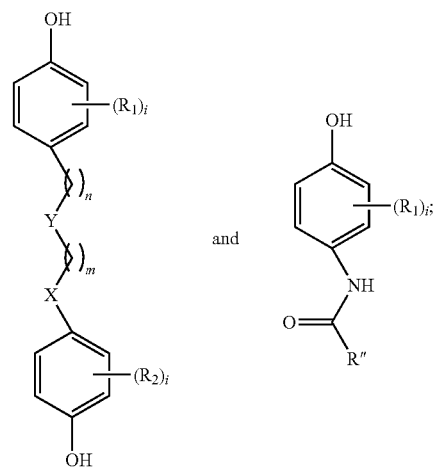

where the vales and preferred values for the variables are as described above.

Suitable phosphorous containing compounds are those which are capable of reacting with phenol containing compounds to produce compounds represented by Structural Formula I-III, including, for example, phosphorous trichloride, phosphorous pentachloride, phosphoric acid and phosphoryl trichloride.

Suitable solvents are those which do not contain any acidic protons and dissolve the starting material and the side products, but do not dissolve the end product. Examples of suitable solvents include, for example, dichloromethane, toluene, tetrahydrofuran, dichloromethane, chloroform, dioxane and acetonitrile.

In certain embodiments, the reaction of the phenol containing compound with the phosphorous containing compound occurs at 25° C. In other embodiments, the reaction of the phenol containing compound with the phosphorous containing compound occurs below 25° C. In other embodiments, the reaction of the phenol containing compound with the phosphorous containing compound occurs at a temperature between 25° C. and 0° C. In other embodiments, the reaction of the phenol containing compound with the phosphorous containing compound occurs at a temperature between 15° C. and 0° C. In other embodiments, the reaction of the phenol containing compound with the phosphorous containing compound occurs at a temperature between 5° C. and 0° C. In other embodiments, the reaction of the phenol containing compound with the phosphorous containing compound occurs at 0° C.

In certain embodiment, the reaction of the phenol containing compound with the phosphorous containing compound takes place under a nitrogen atmosphere.

In certain embodiments the reaction takes place over 5 hours. In certain other embodiment the reaction takes place in less than 5 hours. In certain other embodiments the reaction takes place in one hour. In certain other embodiment the reaction takes place in less than one hour. In certain other embodiments the reaction takes place for a period of 30 to 40 minutes.

In certain embodiment after completion of the reaction the suitable solvent is removed by distillation In certain other embodiments after the suitable solvent is distilled off, the compound of the present invention are purified via crystallization using techniques known in the art.

In certain embodiments, after crystallization, the crystals are further filtered and washed using techniques known in the art.

Scheme 1 is a representative example of the synthesis of a compound of the present invention.

Scheme 1, shows the synthesis of a sterically hindered phenol and phosphite based compound of structural formula I.

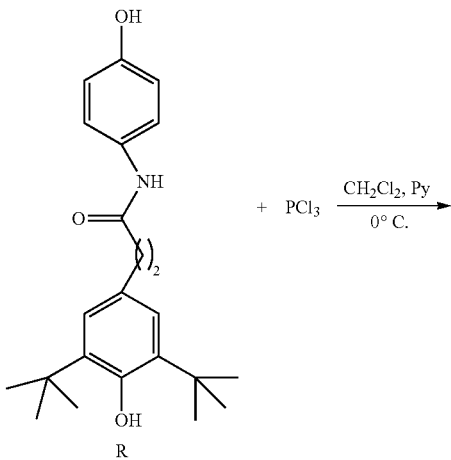

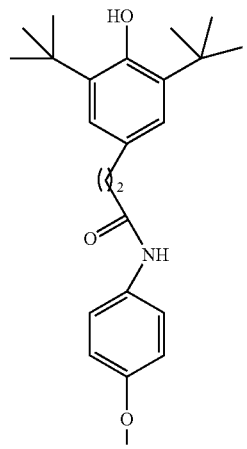

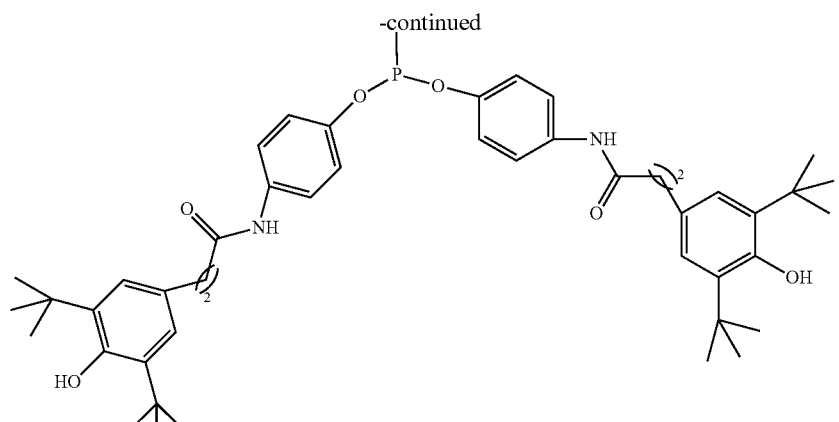

S

The macromolecular antioxidant S was synthesized by one pot reaction of phenol with phosphorous trichloride using dichloromethane as a solvent at 0° C. The yield of the title compound was more than 95%.

Scheme 2, shows the synthesis of a sterically hindered phenol and phosphite based compound of structural formula II.

Scheme 3, shows the synthesis of a sterically hindered phenol and phosphite based compound of structural formula III.

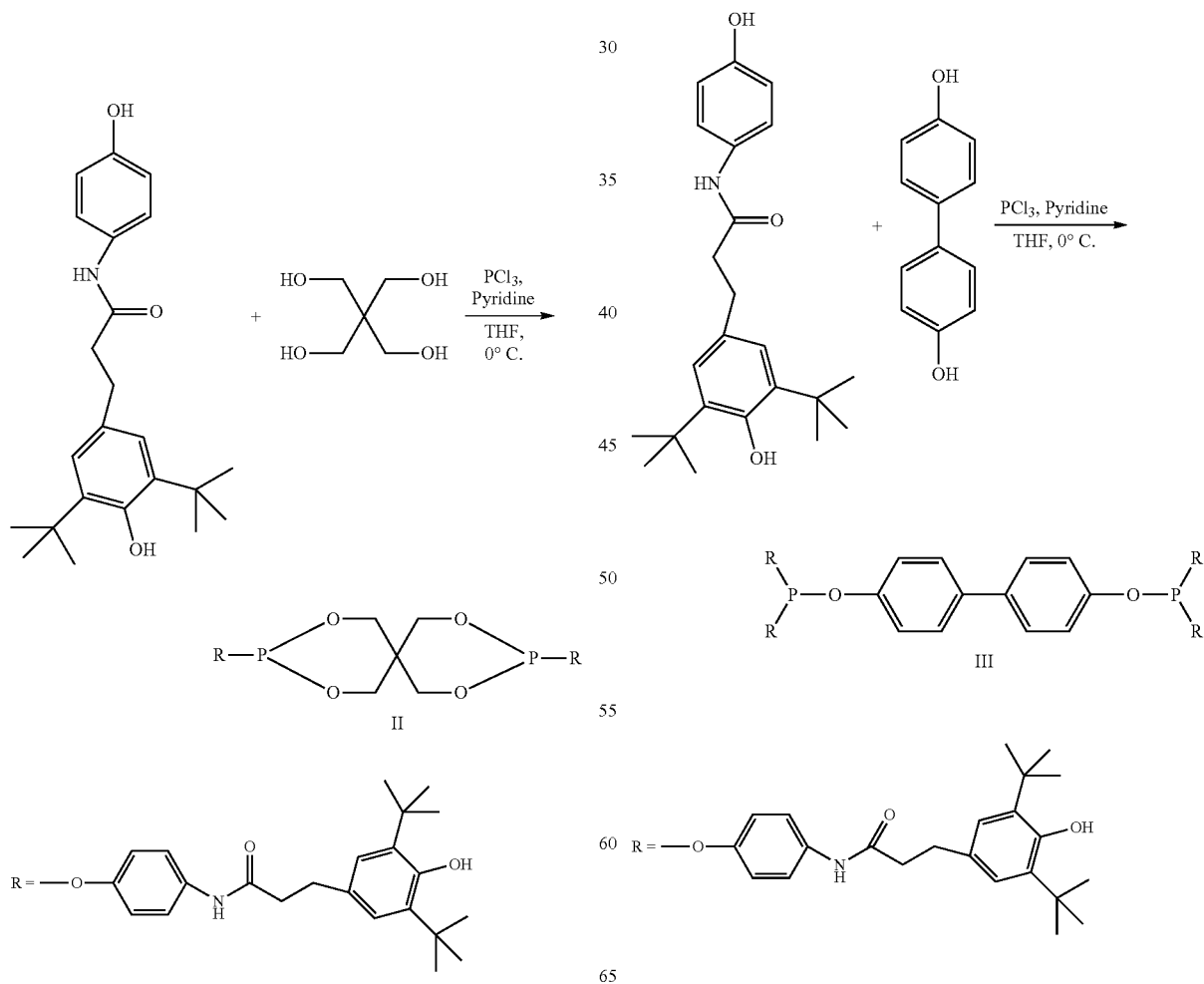

The following is an example of one embodiment of the invention and is not to be considered limiting in any way.

In one embodiment the sterically hindered phenol and phosphate based antioxidant is:

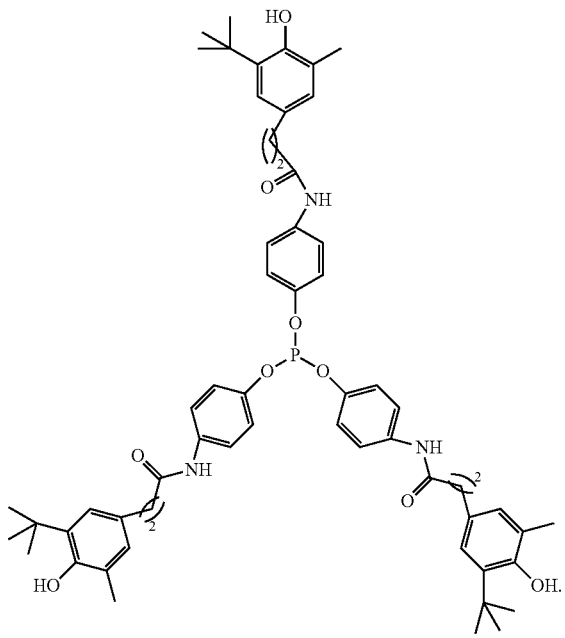

EXEMPLIFICATION

Example 1

Preparation of tris[N-(4-hydroxyphenyl),-3-(2,6-di-tert.-butyl, 4-hydroxyphenyl)propionamide]phosphite, S A 1 L two-necked round bottom flask equipped with a thermometer, a dropping funnel and a nitrogen inlet was charged with 100 g (0.271 mole) of N-(4-hydroxyphenyl)-3-(2,6-di-tert-butyl, 4-hydroxy phenyl) propionamide, 22 ml (0.271 mole) pyridine in 200 ml of dichloromethane. 7.86 ml (9.033 mmol) of phosphorous trichloride was then added dropwise at a temperature of 0 to 5° C. under nitrogen atmosphere for a period of 30 to 40 minutes. After the addition, the funnel was removed and completion of the reaction was checked by TLC/HPLC. After completion, the dichloromethane was distilled out at 40° C. To the residue was added 100 ml of methanol to get white crystalline precipitate, which was then filtered and washed several times with cold methanol. The product was characterized by spectroscopic techniques. The melting point is in the range of 224-245° C.

Example 2

Stabilization of polypropylene by tris[N-(4-hydroxyphenyl),-3-(2,6-di-tert.-butyl, 4-hydroxyphenyl)propionamide]phosphite S 1000 ppm of S was added to unstabilized polypropylene powder and extruded with single screw extruder in the form wires which was then palletized using a pelletizer. The pelltized sample of polypropylene was subjected to an accelerated oxidative stability test using differential scanning calorimetry (DSC) (ASTM D3895 method).

The results are shown in FIG. 1, which shows that tris[N-(4-hydroxyphenyl),-3-(2,6-di-tert.-butyl, 4-hydroxyphenyl) propionamide]phosphite has a significantly higher oxidative induction time than commercially available Irganox® 1010 in polypropylene (PP) at 1000 ppm (extruded at 230° C.). For IRGANOX 1010, the onset Y value is 21.9526 mW and the onset X value is 11.206 minutes. For tris[N-(4-hydroxyphenyl),-3-(2,6-di-tert.-butyl, 4-hydroxyphenyl)propionamide] phosphate, the onset Y value is 23.0327 mW, and the onset X value is 36.221 minutes.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of preventing oxidation comprising combining an oxidizable material with a compound represented by the following structural formula:

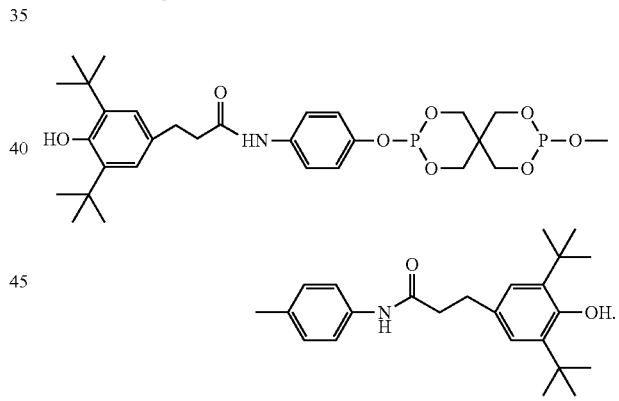

* * * * *